United States Patent [19]

Arnaud et al.

[11] Patent Number: 4,622,517

[45] Date of Patent: Nov. 11, 1986

[54] PORTABLE DEVICE HAVING A PROBE RELEASABLY SUPPORTED ON A MOVABLE CURSOR FOR THE NON-DESTRUCTIVE EXAMINATION OF A SURFACE ALONG A LINE

[75] Inventors: Jean-Louis Arnaud, Verrieres-le-Buisson; Michel Floret, Gennevilliers, both of France

[73] Assignee: Societe Nationale Industrielle et Aerospatiale, Paris, France

[21] Appl. No.: 574,172

[22] Filed: Jan. 26, 1984

[30] Foreign Application Priority Data

Feb. 24, 1983 [FR] France ................................ 83 03044

[51] Int. Cl.⁴ ...................... G01N 27/82; G01R 33/00
[52] U.S. Cl. ........................................ 324/262; 73/633;
  73/661; 324/207; 324/227; 324/243
[58] Field of Search .......................... 324/234, 236–243,
  324/262, 226, 227, 207; 73/618, 633, 634, 661;
  33/503, 556, 557, 572

[56] References Cited

U.S. PATENT DOCUMENTS

| | | | |
|---|---|---|---|
| 3,537,300 | 11/1970 | Rapuzzi | 73/633 |
| 3,588,683 | 6/1971 | Lloyd | 324/241 X |
| 3,611,120 | 10/1971 | Forster | 324/225 |
| 3,617,874 | 11/1971 | Forster | 324/241 |
| 3,898,555 | 8/1975 | Tellerman | 324/34 |
| 4,304,133 | 12/1981 | Feamster | 73/633 |
| 4,423,636 | 1/1984 | Plante | 324/262 X |
| 4,468,620 | 8/1984 | Vaerman | 324/262 X |

*Primary Examiner*—Gerard R. Strecker
*Attorney, Agent, or Firm*—Fisher, Christen & Sabol

[57] ABSTRACT

The invention relates to a portable device for the non-destructive examination of a surface along a line, by means of at least one detection probe displaced along said line and guided by a guide removably fixed on said surface, wherein said guide has a length such that any portion of said line of comparable length presents a negligible variation in curvature, said probe is mounted in a probe-holder adapted to be displaced by hand and connected to said guide in rigid manner parallel thereto and in loose manner transversely to said guide, and means are provided for indicating, at each instant of a displacement of said probe-holder along said guide, the position of the probe-holder on the latter. The invention is particularly applicable to the verification of the riveted joints of aircraft fuselages.

4 Claims, 6 Drawing Figures

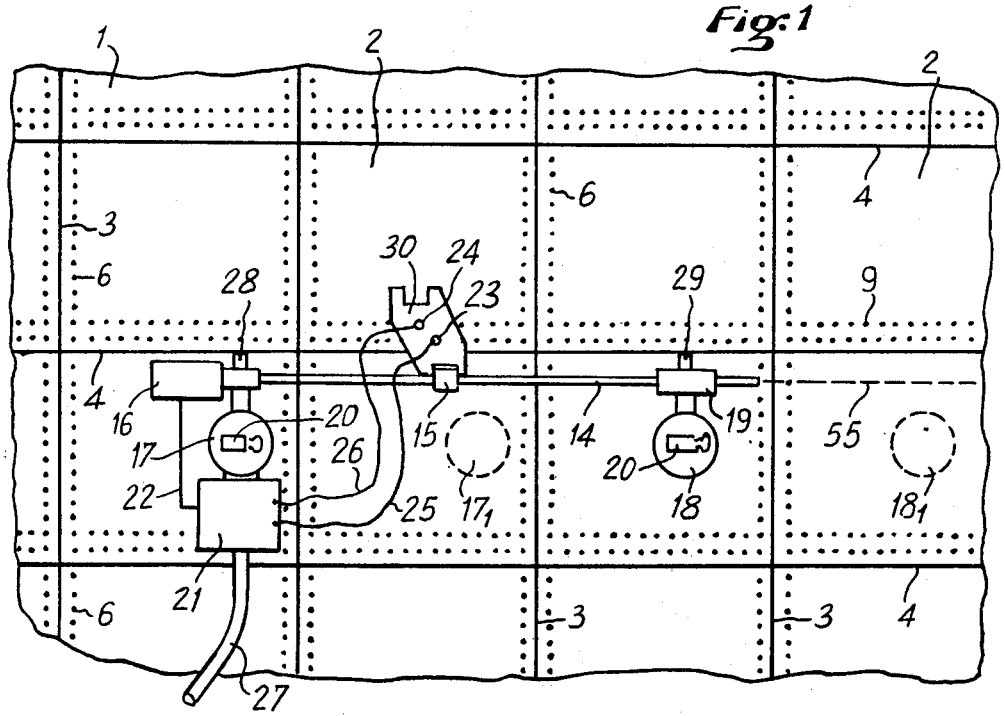
Fig. 1
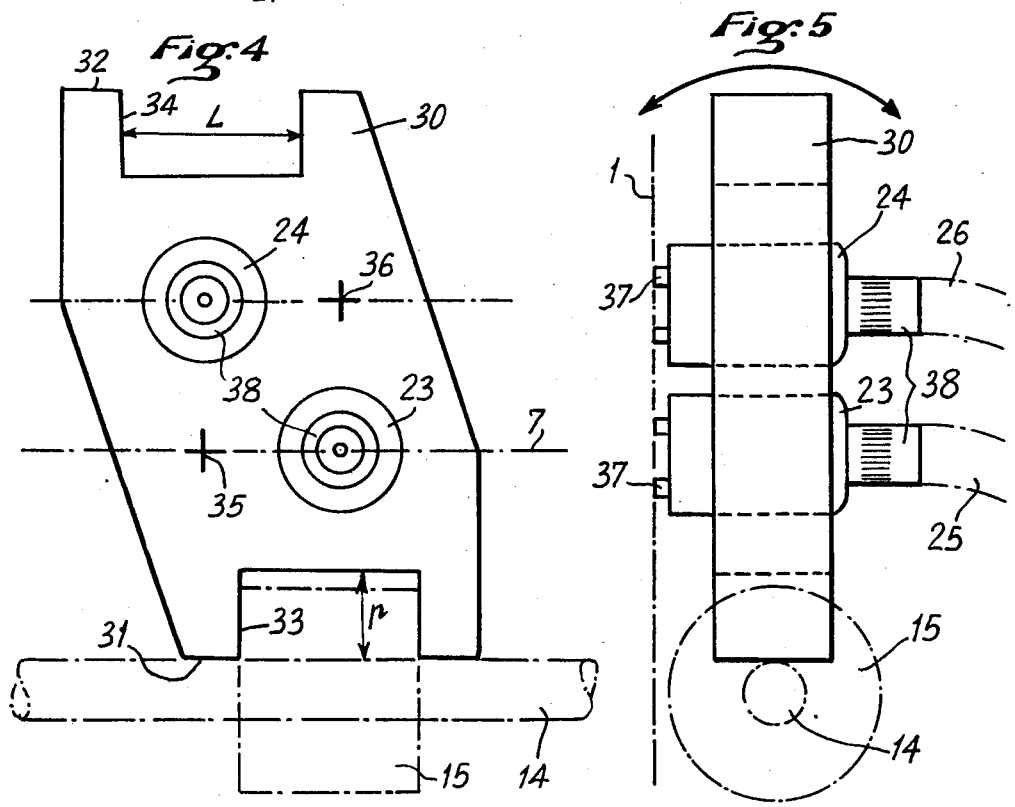
Fig. 4
Fig. 5

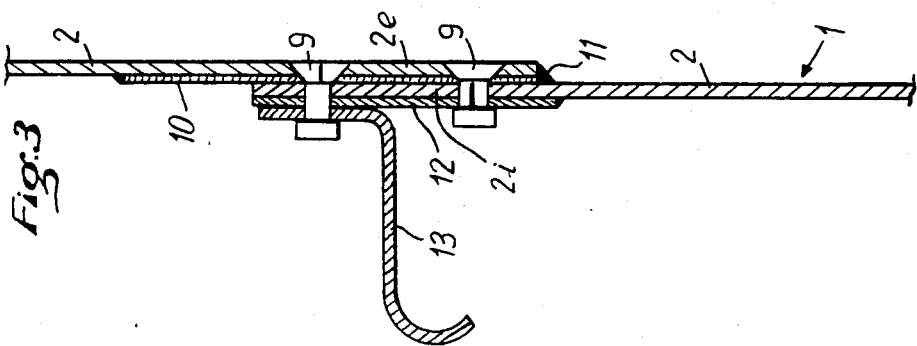
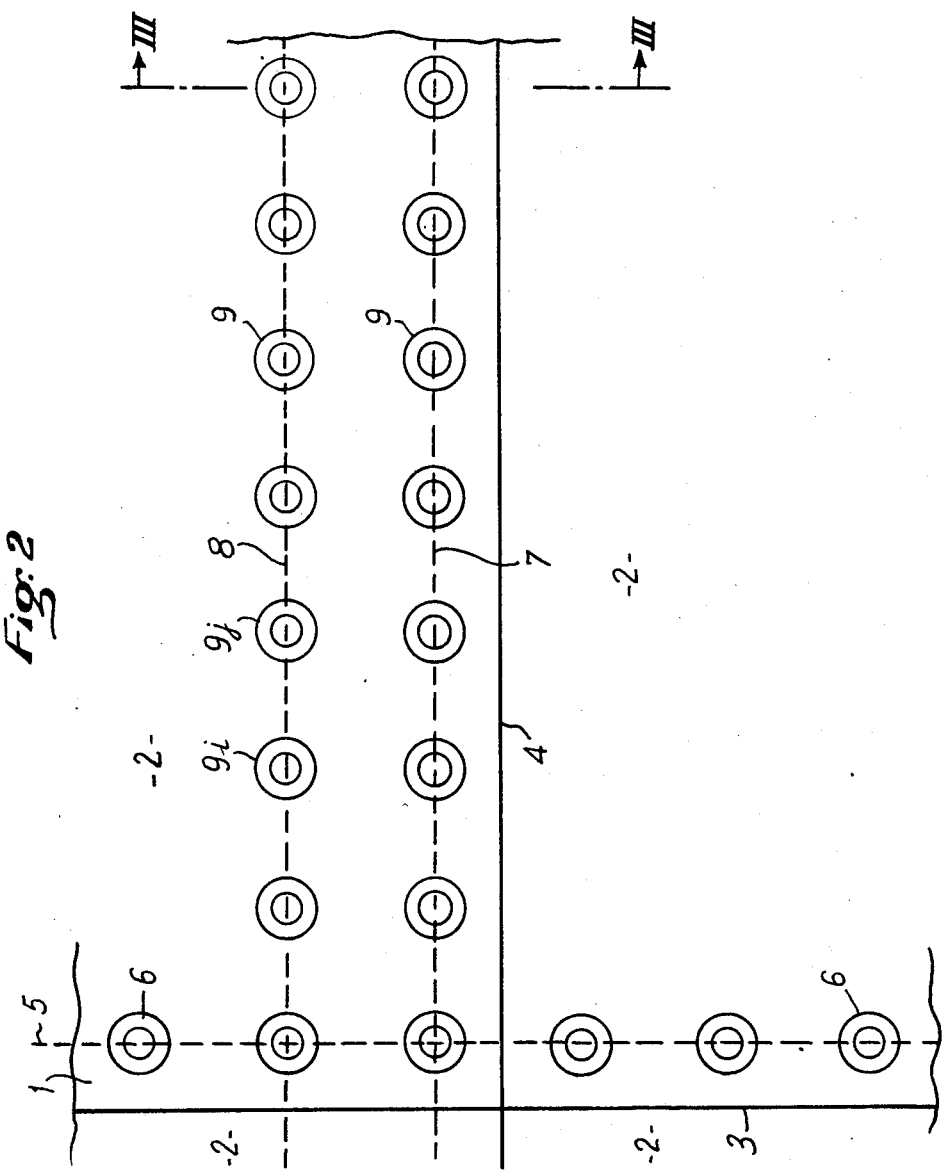

PORTABLE DEVICE HAVING A PROBE RELEASABLY SUPPORTED ON A MOVABLE CURSOR FOR THE NON-DESTRUCTIVE EXAMINATION OF A SURFACE ALONG A LINE

The present invention relates to a portable device for the non-destructive examination of a surface along a line. Although this device may be used in numerous applications such as the non-destructive examination of welds of tubes, pipes, etc . . . , the present invention will be described hereinafter more especially in connection with the non-destructive examination of the joints of the panels constituting the fuselage skin of an aircraft.

The skin of the fuselage of an aircraft is known to be constituted by individual panels riveted together and the longitudinal edges of two adjacent panels overlap in tight manner and are assembled by means of rivets or the like. Such riveted joints suffer from considerable fatigue in the course of use of the aircraft, particularly by reason of the cycles of compression and decompression to which the fuselage is subjected. This may result in the formation of cracks which develop from the holes through which the rivets pass in the panels and the detachment of the edges of the joint. Consequently, the joints weaken and may undergo the attack of corrosion. It is therefore indispensable to monitor said joints periodically in order to know their state as far as the development of the cracks, the detachment of edges and the progress of corrosion are concerned.

The non-destructive examination of the riveted joints of aircraft is generally carried out at present by means of a probe (most often, an ultra-sonic probe) transmitting its signals to a television monitor and to a recorder, an operator displacing the probe from one rivet to the following, by hand. Centering of the probe with respect to the rivet is very important as far as the result of examination is concerned, and the operator must pay constant attention. This results in the operator not being able to watch the television screen at the same time, and errors may be produced. Moreover, such an examination is long and fastidious (the fuselage of a modern wide-body aircraft comprises between 40,000 and 50,000 rivets), this promoting omission or duplication of the monitoring of certain rivets. Finally, the risks of error are increased due to the difficult working conditions for the operator: in fact, the fuselage of a wide-body aircraft is gigantic and the operator is sometimes located more than ten metres above the ground and sometimes underneath the fuselage.

To overcome these drawbacks of manual examinations, it may be envisaged to render the latter automatic, for example by means of guides which would be removably fixed along the joints to be monitored and along which said probe would move under the action of motors or the like. However, it would be difficult, if not impossible, to use such automatic apparatus, because of the variations in curvature which the lines of join present over their length and because of surface defects on the fuselage along said joins.

It is an object of the present invention to overcome the drawbacks of the manual method mentioned above and to render possible partial automation of the process of non-destructive examination, by eliminating the difficulties of an entirely automatic process.

To this end, according to the invention, the portable device for the non-destructive examination of a surface along a line, by means of at least one detection probe displaced along said line and guided by a guide removably fixed on said surface, is noteworthy in that said guide has a length such that any portion of said line of comparable length presents a negligible variation in curvature, in that said probe is mounted in a probe-holder adapted to be displaced by hand and connected to said guide in rigid manner parallel thereto and in loose manner transversely to said guide, and in that means are provided for indicating at each instant of a displacement of said probe-holder along said guide, the position of the probe-holder on the latter.

Thanks to the invention, it is thus possible to scan the whole of said line, section by section, by successive displacements of said device therealong, separated by stop times corresponding to the examination of one of said sections, without suffering the drawbacks of the variations in curvature of the line, since, along each section, such variations are negligible. Furthermore, due to the mode of connecting the probe-holder to the guide, the probe may be manually pressed more or less towards the surface, so as to be able to follow the imperfections of said surface, whilst having a perfectly located position along said guide.

With a view to its removable fixation on the surface, the device according to the invention may comprise manually controllable suction cups. In this case, at least one of said suction cups is advantageously mounted to slide with respect to said guide, so that said guide may be displaced along said line by said suction cups moving alternately towards and away from it in the manner of a caterpillar, one of said suction cups being fixed on said surface and the other being disconnected therefrom in the course of each of said alternate movements.

In an advantageous embodiment, said means for indicating the position of the probe-holder along the guide comprise a cursor capable of moving freely along said guide and a generator furnishing an electrical magnitude representative of the position of said cursor along the guide, and said probe-holder is simply fitted on said cursor. The latter is displaced along the guide via the probe-holder held in an operator's hand.

Such position indicating means may be of the potentiometric type. However, they are advantageously of the type described in U.S. Pat. No. 3,898,555. To be fitted on the cursor, the probe-holder is provided with a recess whose length is such that the probe-holder is a friction fit on the cursor, but the probe-holder can bear pivotally on said guide, which is advantageously of circular section at this end.

Said probe-holder is preferably constituted by a transparent rigid plate provided with cross-hairs. It is thus possible to see the line to be examined through said probe-holder and to centre the probe with respect to a zone of observation (rivet for example) whilst aiming the cross-hairs at another zone (other rivet).

Thanks to the device according to the invention, the operator does not have to give his attention to the positioning of the probe with respect to the line to be examined. Consequently, his attention is free to study an image of this line appearing on a monitor screen. According to a particular feature of the invention, the device comprises a monitoring box, possibly partly fast with said guide, comprising means for adjusting and reading said probe and a microprocessor, a portable display device intended to remain in the vicinity of said device and a plurality of peripheral apparatus intended to be placed at fixed stations at some distance from the surface being examined. The display device enables the operator to follow the examination and possibly to examine a doubtful zone at greater length. He may also return rearwardly, for a complementary examination after having passed over such a zone. The peripheral apparatus are disposed on the ground within reach of another operator and they may comprise a keyboard for introducing data, another display device, a printer, a memory unit, etc . . .

In order to enable the operator manually actuating the probe-holder and the cursor to return rearwardly in the course of a displacement of the probe along the guide, the data coming from the probe and transmitted to said memory unit for one direction of displacement are advantageously erased during a displacment of said probe in opposite direction over the whole extent of said the opposite displacement.

When the operator, after having returned the probe in opposite direction, displaces said probe in the data acquisition direction again, he may thus record fresh data.

When the device according to the invention is intended to examine lap joints of panels comprising two parallel lines of rivets, the probe-holder advantageously comprises two probes of which one is adapted to examine the outer panel along one of said lines of rivets and of which the other is adapted to examine the inner panel along the other line of rivets. The probe-holder may be reversible to be able to occupy two positions for which the two probes change their positions, so that the one which examines one line of rivets for one of the positions examines the other line of rivets for the other position, and vice versa.

Means are preferably provided for positioning the guide with respect to the line of join and the probes with respect to the lines of rivets. Such means may be constituted by fingers abutting on the end edge of the outer panel.

Thanks to the invention, a semi-automatic, manually controlled device is thus obtained.

The invention will be more readily understood on reading the following description with reference to the accompanying drawings in which:

FIG. 1 shows the device according to the invention positioned on a portion of fuselage of an aircraft.

FIG. 2 is a front view, to a larger scale, illustrating the connections between the individual panels of the skin of an aircraft fuselage.

FIG. 3 is a section along line III—III of FIG. 2.

FIG. 4 is an enlarged front view showing the probe-holder and its assembly on the guide rod of the device.

FIG. 5 is a side view corresponding to FIG. 4.

In these Figures, like references designate like elements.

Figure 6:
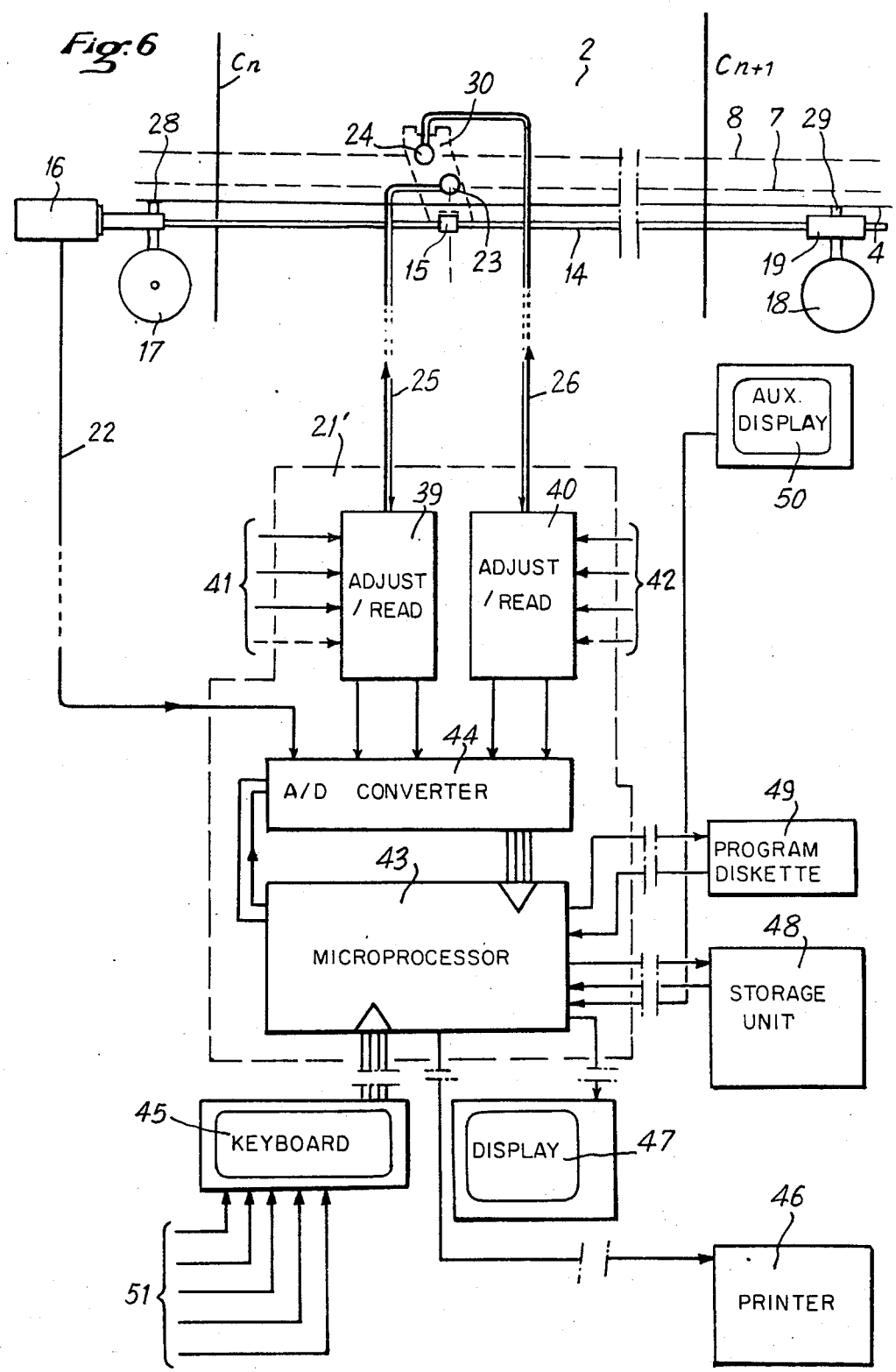
FIG. 6 is the block diagram of the device according to the invention.

Referring now to the drawings, the portion 1 of fuselage skin for aircraft, schematically shown in FIG. 1, is constituted, in conventional manner, by individual rectangular panels 2 assembled together and defining lines of transverse joints 3 and lines of longitudinal joints 4.

The lines of transverse joints 3 correspond to the location of the frames (not shown) of the fuselage and transverse lines 5 of rivets 6 are provided for assembling the transverse edges of the panels 2 on said frames.

As clearly shown in FIGS. 2 and 3, the lines of longitudinal joints 4 are of the lap type and the edges 2e and 2i of two adjacent panels 2 overlap and are assembled by means of two parallel lines 7 and 8 of rivets 9. These overlapping edges 2e and 2i press therebetween a sealing strip 10 and an O-ring 11 is disposed between the end (forming the apparent line of joint 4) of the outer edge 2e and the outer wall of the inner edge 2i. Reinforcing strips and sections 12 and 13 are provided inside the skin 1 of the fuselage and are connected thereto by the lines 7 and 8 of rivets 9.

FIG. 1 schematically shows the device according to the present invention, in the course of verifying the longitudinal lines 7 and 8 of rivets 9 of a panel of skin 2. This device comprises a guide rod 14 whose length corresponds to that of a few panels 2, for example to the length of 2 or 3 panels 2, and on which a cursor 15 may slide. It further comprises, at one of its ends, a measuring box 16, capable of indicating at each instant the position of the cursor 15 along the rod 14. The assembly 14-15-16 is for example of the type described in U.S. Pat. No. 3,898,555.

With this assembly 14-15-16 are associated two suction cups 17 and 18 of known type, actuatable by a manual lever 20. Suction cup 17 is rigidly connected to the measuring box 16, whilst suction cup 18 is fast with a slide block 19 adapted to slide along the guide rod 14.

The device according to the invention further comprises a control box 21, secured to suction cup 17 and receiving the measurements from box 16, via the link 22 and the indications from probes 23 and 24, via links 25 and 26. The box 21 is connected by a link 27 to a plurality of peripheral apparatus, as shown in FIG. 6, in which a more complete variant embodiment 21' of the box 21 is shown separate from suction cup 17.

Furthermore, it goes without saying that, a part of the elements of the box 21' may be secured to the assembly 14-15-16 (like box 21), the rest being separated therefrom and being connected thereto by link 27 (like box 21').

Fingers 28 and 29, respectively secured to the box 16 and the slide block 19, may cooperate with the end of the outer edge 2e and/or with the joint 11 in order to dispose the guide rod 14 parallel to the line of joint 4, and therefore to lines 7 and 8 of rivets 9 to be examined.

The probes 23 and 24 are borne by a probe-holder 30 which is advantageously constituted by a thick transparent plate, for example made of a methacrylic compound in which said probes are incorporated. In two of its opposite edges 31 and 32, the probe-holder 30 comprises two identical notches 33 and 34 whose length L is such that they may fit with gentle friction on the cursor 15 and whose depth 1 is such that, when they are fitted on the cursor 15, the edge 31 (or edge 32) is in abutment on the guide rod 14. In plate 30, the probes 23 and 24 and the two notches 33 and 34 are offset, parallel to the guide rod 14, so that, on the one hand, when the notch 33 is fitted on the cursor 15 and the edge 31 is in abutment on the guide rod 14, the probe 23 is centred on the rivet 9j, of row j, of line 7, if the probe 24 is centred on rivet 9i, of row i, of line 8, and that, on the other hand, when the notch 34 is fitted on the cursor 15 and the edge 32 is in abutment on the guide rod 14, the probe 24 is centred on the rivet 9j, of line 7, if the probe 23 is centred on rivet 9i of line 8.

The probe-holder 30 further comprises two cross hairs 5 and 36, centred respectively on rivet 9i of line 7 and on rivet 9j of line 8, when the probes 23 and 24 are respectively centred on the rivet 9j of line 7 and on rivet 9i of line 8.

In the direction of the skin 1 of the fuselage, the probes 23 and 24 are provided with bearing and sliding pads 37, whilst, on the opposite side, they comprise sockets 38 for connection to links 25 and 26.

As shown in FIG. 6, the control box 21' comprises means 39 and 40 respectively for adjusting and reading the probes 23 and 24, connected thereto by links 25 and 26. These adjusting and reading means are provided with control inputs 41 and 42 respectively. For example, if the probes 23 and 24 are of the eddy current type, the control inputs 41 and 42 may concern the frequency, the gain, the phase of operation as well as a trigger threshold. Moreover, the control box 21 comprises a microprocessor 43, in liaison with the outputs of said adjusting and reading means 39 and 40, via an analog-to-digital converter 44. The latter may also convert the data coming from the measuring box 16, to send it in suitable form to the microprocessor 43.

The microprocessor 43 is furthermore in liaison with a keyboard 45, a printer 46, a display device 47, a storage unit 48, for example of the hard disc type, a programn diskette 49 and another display device 50 in the vicinity of the operator ensuring displacement of the probe.

As mentioned above, even when the control box 21 is secured to the assembly comprising the elements 14 to 20 and 22 to 30, due to the low weight of said box, the assembly of elements 14 to 30 is portable and may be at the disposal of a first operator moving, in one manner or another, with respect to the skin 1 of the fuselage, in the vicinity thereof. The display device 50, which may also be portable and of small dimensions, is also at the disposal of this first operator. On the other hand, all the other peripheral apparatus 45 to 49 may be disposed far from the place where the riveted joints are verified and they are for example placed on the ground, at the disposal of a second operator. The different connections between the control box 21' and the peripheral apparatus 45 to 49 are assembled in the link 27 shown in FIG. 1.

To effect a systematic verification of all the longitudinal joints 4 (for example) of an aircraft, a number is firstly attributed to each section of the aircraft, to each frame of the fuselage (corresponding to the joints 3) and to each joint 4.

The first operator who is located near a portion of joint 4 to be verified disposed between frames $C_n$ and $C_{n+1}$ and which bears the assembly of elements 14 to 30 and the display device 50, fixes the suction cups 17 and 18 on the skin 1 so that they are located on either side of said frames and that the fingers 28 and 29 abut against the joint 11. It is then sure that the rod 14 is parallel to this portion of joint 4 and that the probes 23 and 24 will respectively lie opposite lines 7 and 8. During this time, the second operator enters, via keyboard 45, various data 51, such as the number of the aircraft, the number of the section of fuselage, the numbers of the frames limiting the portion of joint 4, the number of the joint 4, the side (left or right) of the fuselage, etc . . . , for identifying each section of joint.

By inputs 41 and 42, the probes 23 and 24 are adjusted, for example for the probe 23 (line 7) to monitor the cracks likely to be produced from holes through which the rivets 9 pass in the inner edge 2$i$ and for probe 24 (line 8) to monitor the cracks likely to be formed from the holes through which rivets 9 pass in the outer edge 2$e$. If probes 23 and 24 are eddy current probes, such an adjustment is effected by variation of carrier frequency, since the depth of the measurement of such a probe is the greater as the operational frequency is lower. Moreover, it will be noted that, if the probe-holder 30 is turned over, whilst the probes 23 and 24 are adjusted in the manner described herein-above, the device according to the invention is then capable of monitoring the cracks likely to be produced from the holes through which rivets 9 pass in the inner edge 2$i$ along the line 8 and in the outer edge 2$e$ along line 7.

The first operator begins by moving the cursor 15/probe-holder 30 assembly towards one of the ends of the section of joint 4 to be monitored and, with the aid of one of the cross hairs 35, 36, he sights the centre of an end rivet 9 so that the probe 23 or 24 standing back more with respect to the corresponding frame is superposed on the first of the rivets 9 of line 7 or of line 8 of said section. He then carries out the same operation at the other end of said section. Subsequently, the microprocessor 43 receives from the measuring box 16 the respective abscissae of these two sights, and, by subtraction, it deduces therefrom the distance separating the frames $C_n$ and $C_{n+1}$ and serving as measuring window for said probes 23 and 24.

The first operator then slides the probe-holder 30 and the cursor 15 manually along the guide rod 14, from one of said frames $C_n$ or $C_{n+1}$ to the other, maintaining the slide pads 37 in abutment against the skin 1. The probes 23 and 24 therefore scan, successively and respectively, the lines of rivets 7 and 8. Due to the difference in the materials constituting the panels 2 (aluminium) and the rivets 9 (titanium), whenever a probe 23 or 24 passes in front of a rivet, it emits a pulse. The number of pulses obtained possibly enables the rivets of the sections of lines 7 and 8 being examined to be counted.

It will be noted that, by comparing the distance separating the frames $C_n$ and $C_{n+1}$ and the numbers of the rivets 9, measured in the manner described hereinabove, with corresponding magnitudes previously memorized, the microprocessor 43 is capable of detecting any error of identification of the section 4 examined.

Furthermore, the first operator does not have to give all his attention to centering the probes 23 and 24 with respect to the rivets 9. He may therefore monitor the images appearing on the screen of device 50, and therefore sees thereon the image of the different rivets of the section and the image of the possible cracks. Similarly, the second operator sees the same images on the screen of device 47. In the event of abnormalities or ambiguities, the first operator may return the cursor 15 and the probe-holder 30 rearwards, maintaining the pads 37 in abutment on the skin 1 and take his time to examine the corresponding zone.

Of course, the information producing the images on the screens of devices 47 and 50 is memorized in the storage unit 48 and printed out on a support by the printer 46.

After having carried out this series of measurements, the first operator possibly turns the probe-holder 30 over to scan lines 7 and 8 with different depths.

When the examination to be carried out on a section of joint 4 is terminated, the first operator inhibits action of the suction cup 17 (by action on lever 20) and he may therefore slide the assembly 14 to 17 towards the suction cup 18, which remains connected to the skin, since in that case the rod 14 may slide along its axis 55 in the fixed slide block 19. He may bring the released suction cup 17 into position 17₁ (cf. FIG. 1), then fix it on the skin 1 in this position by actuating the lever 20. He then actuates the lever 20 of suction cup 18 for disconnection purposes and he may slide assembly 18-19, in the same direction as previously for suction cup 17, to bring suction cup 18 into position 18₁. The device according to the invention is then ready for examination of the panel 2 adjacent the one which has just been described.

By successively moving the suction cups 17 and 18 towards and away from the skin, it is thus possible to displace the device along axis 52 of the guide rod 14 in order to examine the whole of the joint 4. Of course, upon each displacement of the device, care is taken that the fingers 28 and 29 remain in abutment against joint 11.

It will be noted that:

the guide rod 14 has a length at the most equal to several times the distance separating two consecutive frames, i.e. to several times the length of an individual panel 2, so that the device according to the invention is particularly well adapted to the variations in curvature of the fuselage and the line of join 4, along its whole length;

the connection of the probe-holder 30 with the cursor 15 by simple fit makes it possible to obtain both a high rigidity of connection between them parallel to the guide rod 14 and a considerable freedom of the probe-holder 30 with respect to the cursor 15, transversely to said guide rod 14; consequently, the position of probes 23 and 24 is defined with high precision, but in the event of roughness on the skin 1, the first operator may reduce his manual pressure on the probe-holder 30 so that the pads 37 pass without catching. In FIG. 5, the transverse freedom of the probe-holder 30 with respect to the cursor 15 is indicated by a double arrow, symbolizing the freedom of rotation of said probe-holder about its bearing on the guide rod 14;

the first operator may study the examination on his monitor screen 50 and, thanks to the possibility of displacement of the probe-holder 30 in both directions, this operator may go in reverse in order to examine a doubtful zone or eliminate an ambiguity. In order not to record several data for the same abscissa along the guide rod, the microprocessor 43 records information in its memory 48 only for one direction of displacement of the cursor 15 on the rod 14 and erases from this memory the information which is already contained therein, when the cursor 15 moves in the opposite direction, in register with the amplitude of said reverse displacement;

despite its simplicity, the device according to the invention presents a high yield, enabling the duration of the monitoring examinations to be divided by a factor of 100, whilst introducing considerable reliability and reproducibility.

Although the Figures have shown a rectilinear guide rod 14, it is obvious that the present invention is not limited to this form of embodiment. When it is desired to examine lines 5 of rivets 6 parallel to the frames of the fuselage, it is obviously necessary to use a curved guide, adapted to the section of the fuselage.

What is claimed is:

1. A portable device for the non-destructive examination of points of a surface distributed along a line on said surface, said device comprising:

at least one probe for producing an output signal that is used for the examination of one of said points;

an elongated guide means having means for releasably securing said guide means to said surface parallel to said line, said guide means having a length equal to a portion of said line, said portion of said line having a negligible variation of curvature;

a cursor mounted for free sliding movement along said guide means and free rotational movement about said guide means;

measuring means fixed to said guide means for indicating at each moment the positions of said cursor along said guide means;

a probe-holder having means for receiving said probe, said probe-holder being releasably mounted to said cursor such that said cursor and said probe-holder slide and rotate together relative to said guide means to allow said probe to be pressed manually towards said surface by an operator; and to allow said probe-holder to be manually displaced along said guide means with said cursor by the operator, and said probe-holder having sighting means for allowing said probe-holder to be aligned with said points by the operator;

said means for releasably securing said guide means having two suction cups each of which is capable of being manually controlled so as to be secured to said surface or released therefrom, at least one of said suction cups being mounted to slide with respect to said guide means, and the other of said suction cups being connected to said guide means so that said guide means may be displaced along said line by releasing one of said suction cups from said surface, moving said one suction cup parallel to said line, re-securing said one suction cup to said surface, releasing the other of said suction cups from said surface, moving said other suction cup parallel to said line, and re-securing said other suction cup to said surface, said guide means being moved parallel to said surface with said movement of one of said suction cups.

2. A portable device for the non-destructive examination of a lap joint comprising an outer panel and an inner panel joined by two lines of rivets, comprising:

two probes each for producing an output signal that is used for the examination of one of said lines of rivets;

an elongated guide means having means for releasably securing said guide means to said surface parallel to said line, said guide means having a length equal to a portion of said line, said portion of said line having a negligible variation of curvature;

a cursor mounted for free sliding movement along said guide means and free rotational movement about said guide means; measuring means fixed to said guide means for indicating at each moment the positions of said cursor along said guide means;

a probe-holder having means for receiving said probe, said probe-holder being releasably mounted to said cursor such that said cursor and said probe-holder slide and rotate together relative to said guide means to allow said probe to be pressed manually towards said surface by an operator; and to allow said probe-holder to be manually displaced along said guide means with said cursor by the operator, and said probe holder having sighting means for allowing said probe-holder to be aligned with said points by the operator; and one of said probes being mounted on the probe-holder in a position adapted to examine the outer panel along one of said lines of rivets and the other of said probes being mounted on the probe-holder in a position adapted to examine the inner panel along the other line of rivets.

3. The device of claim 2 wherein the probe-holder may be releasably secured to said cursor in two different positions such that shifting the probe-holder from one to the other of said positions will cause the two probes to interchange their positions so that the probe which examines one of said lines of rivets when the probe-holder is secured to the cursor in one of said positions examines the other of said lines of rivets when the probe-holder is secured to the cursor in the other of said positions, and vice versa.

4. The device of claim 2 or 3 further comprising means for positioning the guide means with repect to the line along which said inner and outer panels are joined and for positioning the probes with respect to the lines of rivets.

* * * * *